United States Patent [19]

Small

[11] Patent Number: 4,713,077

[45] Date of Patent: Dec. 15, 1987

[54] METHOD OF APPLYING A CHIN IMPLANT, DRILL GUIDE TOOL AND IMPLANT

[76] Inventor: Irwin A. Small, 6861 Orinoco Cir., Brimingham, Mich. 48010

[21] Appl. No.: 812,281

[22] Filed: Dec. 23, 1985

Related U.S. Application Data

[63] Continuation-in-part of Ser. No. 702,595, Feb. 19, 1985, Pat. No. 4,608,972.

[51] Int. Cl.$^4$ ............................................. A61F 2/30
[52] U.S. Cl. ................................ 623/16; 128/92 VD
[58] Field of Search .......... 128/92 V, 92 VY, 92 VD; 623/16–23; 433/75–76

[56] References Cited

U.S. PATENT DOCUMENTS

| D.270,373 | 8/1983 | Straith | 623/20 |
| 3,589,011 | 6/1971 | Sneer | 623/16 |

FOREIGN PATENT DOCUMENTS

| 0179626 | 4/1986 | European Pat. Off. | 623/18 |
| 1961531 | 7/1970 | Fed. Rep. of Germany | 623/16 |
| 2378505 | 9/1978 | France | 623/20 |
| 2447182 | 9/1980 | France | 623/11 |
| 8302555 | 8/1983 | PCT Int'l Appl. | 623/18 |

Primary Examiner—Richard J. Apley
Assistant Examiner—David J. Isabella
Attorney, Agent, or Firm—Cullen, Sloman, Cantor, Grauer, Scott & Rutherford

[57] ABSTRACT

The method of applying a chin implant to a human includes stripping tissues from the lower jaw mandible to the jawbone, locating, applying and supporting a drill guide against the exposed bone at a median plane, drilling through the drill guide a pair of laterally spaced bores into the jawbone equidistant from the median plane, threading a headless cortical screw having an axial bore into each of the drilled bores, and assembling a chin implant with a pair of mount posts snugly against the jawbone while guidably positioned the posts into the screws, and suturing the stripped tissue back into normal position enclosing and retaining the implant. The drill guide has a handle with a central axis mounting a body engageable with the exposed jawbone including a locating center on its axisregisterable with the medium plane. The body has a pair of laterally spaced drill guide bores and a pair of laterally spaced chin engaging arms so that symmetrical bores can be drilled into the jawbone. The chin implant assembly includes a pair of laterally spaced cortical screws with axial bores threaded fully into the exposed jawbone. A formed implant of resilient material engages the exposed jawbone and a pair of mount posts are retained in the implant and guidably positioned within the cortical bone screws.

15 Claims, 12 Drawing Figures

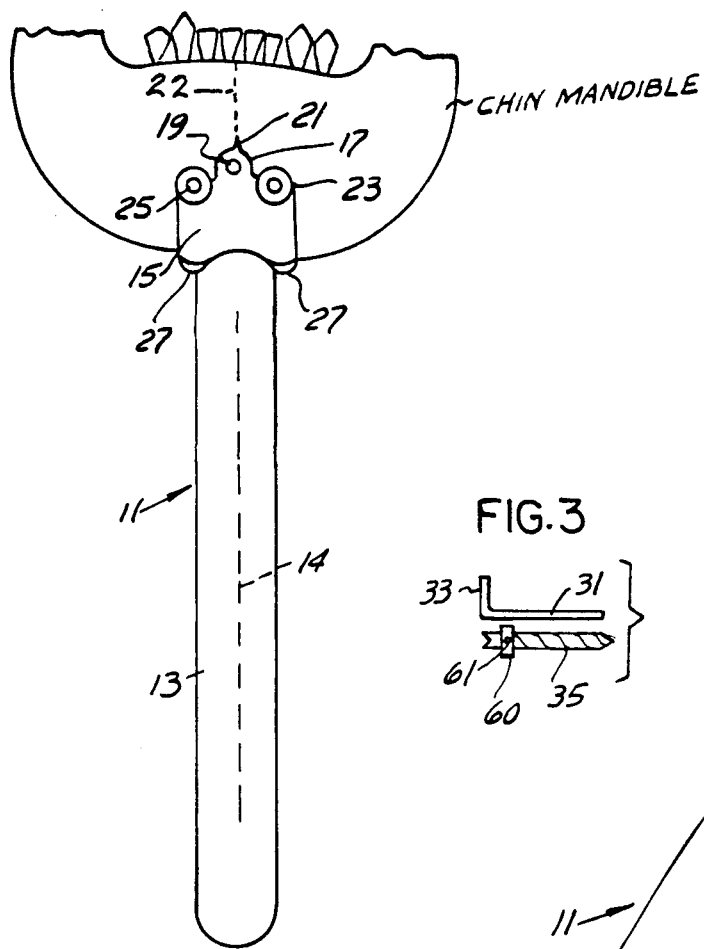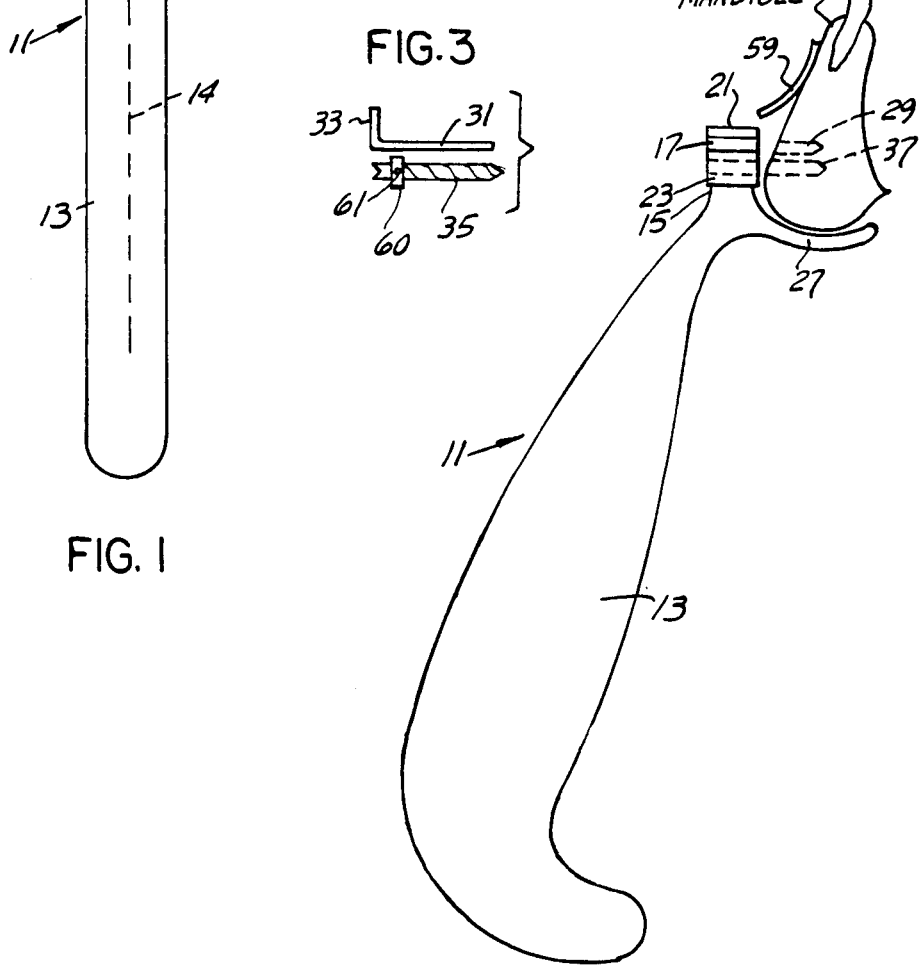

METHOD OF APPLYING A CHIN IMPLANT, DRILL GUIDE TOOL AND IMPLANT

RELATED APPLICATION

This is a continuation-in-part of my copending patent application Ser. No. 702,595 filed Feb. 19, 1985 now U.S. Pat. No. 4,608,972.

The present invention is directed to the method of applying a chin implant to a human mandible including a series of steps, and employing an apertured drill guide for the accurate location and the drilling of a pair of laterally spaced bores into the jawbone, a chin implant assembly which includes a pair of cortical screws threaded into bores within the jawbone onto which there is assembled a resilient chin implant and to engage the exposed jawbone having a pair of mount posts guidably positioned within the screws.

BACKGROUND OF THE INVENTION

Heretofore chin implants of a resilient material have been applied to the exposed mandible bone and retained in position by the reassembled skin tissue which encloses and retainingly engages the implant. One difficulty has been that during and after healing, the implants have been known to slip and become mechanically displaced from the desired central location. In some instances, the pressure of the retaining skin upon the implant has resulted in resorption or migration of the implant partly into the bone, sometimes referred to as bone resorption.

THE PRIOR ART

Methods of providing a mandibular staple for the human jawbone for anchoring a lower denture upon a mandible together with a drill guide therefore are shown in one or more of the following United States Patents of the Inventor herein:

| U.S. Pat. No. | NAME | DATE |
| --- | --- | --- |
| 3,414,975 | Irwin A. Small | 12/10/68 |
| 3,664,022 | Irwin A. Small | 5/23/72 |
| 3,895,444 | Irwin A. Small | 7/22/75 |
| 4,439,152 | Irwin A. Small | 3/27/84 |

SUMMARY OF THE INVENTION

An important feature of the present invention is to provide an improved method including a series of steps for the application of a chin implant to the human mandible and wherein the assembled implant is accurately and positively located and retained against accidental lateral translation.

Another feature is to provide an improved implant assembly which eliminates bone resorption or migration of the implant into the bone and provides for osteointegration which is an intimate bone to metal interfacing about the hollow bone screw. The hollow bone screw allows for insertion of the chin implant into the screws which accurately locates the implant and prevents migration. The chim implant provides an improved bond and interlock of bone tissue into the chin implant which has an inner facing surface of a Dacron Velour for a biomechanical interlocking of the inner surface of the implant against the jawbone and with respect to migrating tissue thereof.

The present invention includes a series of steps including surgically stripping away tissue from frontal portions of the lower jaw (mandible) adjacent to the chin and down to the jawbone and thereafter centrally locating and applying an apertured drill guide to the exposed bond and to the undersurface of the chin upon a central axis aligned with the median plane of the mandible, thereafter drilling through the drill guide, first a central locating bore and then a pair of laterally spaced bores into the jawbone equally spaced with respect to the median plane and at a predetermined distance above the bottom of the mandible, successively threading a headless cortical bone screw into each of the bores within the mandible until the outer end of the screw is in registry with the outer surface of the jawbone and successively assembling a resilient chin implant with a pair of projecting mount posts snugly against the bone while slidably positioning and retaining the posts within the screws and thereafter suturing the tissue back into normal position enclosing and retainingly engaging the implant.

Another feature is to provide an improved drill guide which has a handle having a central vertical axis, which mounts an apertured body engagable with the exposed jawbone and which includes a locating center and locking pin registerable with the median plane of the mandible. The guide has a pair of laterally spaced drill guide bores and a pair of laterally spaced chin engaging arms that fit underneath the chin so that symmetrical bores can be drilled into the jawbone.

A further feature includes a chin implant assembly which includes a pair of laterally spaced cortical screws having axial bores, threaded in compression into pre-drilled bores within the jawbone together with a chin implant of resilient material which engages the exposed bone and includes a pair of embedded mount posts guidably projected and retained within the cortical screws.

As another feature the mount posts are initially separate from the implant and at their one ends are projected into the cortical screws. The implant has a pair of spaced bores adapted to snugly receive the other ends of the mount posts.

As another feature the respective cortical screws are self threading, are headless having a uniform exterior diameter, a longitudinal bore which opens to one end of the screw and which includes a hexagonal aperture to receive a tool or wrench for threading the screws into the bores drilled into the jawbone.

Another feature includes an improved resilient performed jaw implant of silicone rubber, polyethylene or hydroxylapatite or other biologically acceptable material together with a pair of mount posts of metal, polyethylene or other biologically acceptable metal compatible with the screws, embedded within the molded implant and adapted for projection into the cortical screws anchored within the jawbone.

Another feature of the improved chin implant includes thereon a formed fontal facing adapted for corresponding registry with the curvature of the exposed mandible and to which has been bonded a facing of Dacron Velour wherein upon healing, there is a biomechanical locking of the inner surface of the implant with respect to bone tissue which has migrated into the facing.

These and other features and objects will be seen from the following Specification and claims in conjuction with the appended drawings.

THE DRAWINGS

FIG. 1 is a front elevational view of the present apertured drill guide as applied to lower portions of a jawbone mandible fragmentarily shown broken away.

FIG. 2 is a right side elevational view thereof in registry with portions of the lower jaw mandible.

FIG. 3 illustrates schematically a locking pin and the twist drill employed, selectively guided through the respective bores of the drill guide for forming corresponding bores within the exposed jawbone and the locking pin for supporting and retaining the drill guide against the jawbone during drilling.

Figure 4:
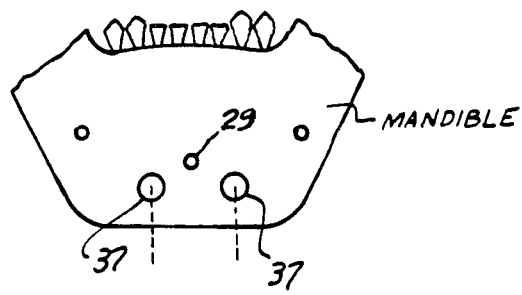
FIG. 4 is a fragmentary frontal view of the lower jaw mandible showing the bores formed therein utilizing the present drill guide.
Figure 5:
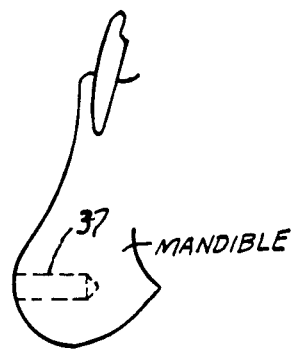
FIG. 5 is a fragmentary side elevational view thereof.

It will be understood that the above drawings illustrate merely the preferred steps of the present method for applying a chin implant, the preferred construction of the drill guide, the chin implant and cortical screw, as one embodiment of the present invention and that other steps and embodiments are contemplated of the scope of the claims hereafter set forth.

DETAILED DECRIPTION OF AN EMBODIMENT OF THE INVENTION

The present drill guide 11 is shown in the drawings, FIGS. 1, 2 and 3, includes a formed handle 13 having an upright central axis 14, when in use, and thereover at one end stabilizing body 15. On the top of said body and forming a part thereof is a top drill guide sleeve 17 having a bore 19 therethrough adapted to receive a drill, such as shown in FIG. 3 having a diameter of approximately two millimeters for illustration and overlying the guide sleeve 17 forming a part of body 15 is a converging locating center 21 arranged along the central axis 14.

The body 15 includes below guide sleeve 17 a pair of laterally spaced drill guide sleeves 23 with bores 25 therethrough adapted to receive a power operated twist or other drill 35, FIG. 3. In this case the twist drill is 2.7 mm, for illustration, and wherein the bores 25 are of sufficient diameter to loosely and guidably receive said drill. In the illustrative embodiment the bores 25 in head 15 are arranged upon opposite sides of axis 14 equidistantly therefrom and between center lines are arranged at a spacing of 12 mm, for illustration.

At the bottom of drill guide body 15 are a pair of laterally spaced forwardly extending downwardly arcuate stabilizing arms 27, similarly spaced apart at their centers at 12 mm, approximately, FIGS. 1 and 2. The respective stabilizer arms are generally spaced below the axis of the respective bores 25, a distance of 12 mm, for illustration, thereby locating the drill guide bores 25 approximately 6 mm above the undersurface of the mandible shown, fragmentarily in FIGS. 1 and 2.

Figure 10:
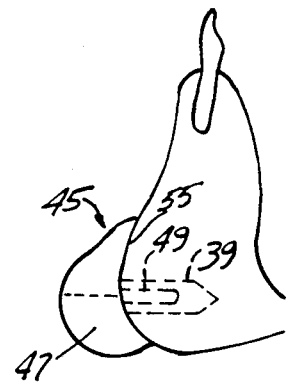
FIG. 10 is a side elevational view of the jaw mandible with the chin implant applied to the exposed jawbone.

As an initial step the present method of applying an implant 45 to the chin of a human mandible, FIG. 10, includes surgically stripping tissue from frontal portions of the lower mandible adjacent the chin, down to the jawbone, as shown schematically in FIGS. 1 and 2, at 59.

This is followed by centrally locating and applying the drill guide 11 to the exposed bone and with the stabilizing arms 27 bearing against the undersurface of the chin. The central axis 14 of the drill guide is in alignment with a median or saggital plane 22 of the lower mandible of a human, fragmentarily shown in FIG. 1.

A further successive step includes drilling through the guide bore 19, utilizing a power drill 35 or hand operated drill, which loosely and guidably projects through bore 19 and into the exposed jawbone of the mandible forming the bore 29, FIG. 2.

Before drilling, the drill guide 11 by manually supporting the handle 13 in an upright position is in snug registry with forward portions of the exposed bone of the mandible. Pointer 21 is in registry with the median plane 22, which now corresponds to the longitudinal upright axis 14 of handle 13. At the same time, the respective stabilizing arms 27 snugly underlie portions of the human chin to provide the correct locating position for the bore 29.

A further step includes projecting the removable locking pin 31 having a transverse head 33 through the top bore 19 of the drill guide and snugly into the mandible bore 29 further supporting and retaining the drill guide in the centralized position shown in FIG. 1, for the subsequent drilling step.

In the illustrative embodiment the locking pin has a diameter of two mm, adapted for snug supporting projection through drill guide bore 19 and into the previously drilled bore 29 in the mandible for suspending the drill guide in an accurate centralized location relative to mandible median 22, FIG. 1.

This is followed by the step of drilling through the guide bores 25 in the drill guide head 15 using a drill 35, FIG. 3, a pair of laterally spaced bores 37 into the exposed jawbone or mandible, FIGS. 2, 4, 5 and 10. In the illustrative embodiment the twist drill 35, FIG. 3, is 2.7 mm, approximately, for drilling the bores 37 of approximately the same diameter into the mandible.

By the use of the present drill guide, it is assured that the laterally spaced bores 37 are arranged equidistant from and upon opposite sides of mandible median 22 and are spaced apart, 12 mm, for illustration. In the illustrative embodiment, the bores 37 are 9 mm in length, approximately, and 2.7 mm in diameter and are arranged 6 mm up from the lower border of the chin mandible, for illustration. The control of the depth of the bore is provided by a drill stop 60 attached to the twist drill by means of a set screw 61.

Figure 6:
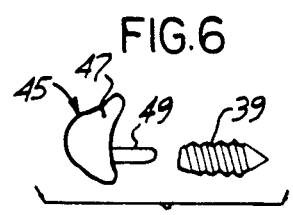
FIG. 6 is a bracketed telescoped view of the cortical screw and the chin implant.
Figure 8:
FIG. 8 is an end view thereof.
Figure 7:
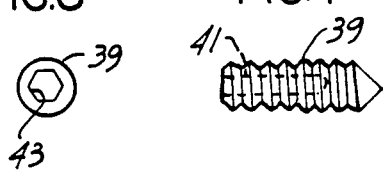
FIG. 7 is a side elevational view of a cortical screw, on an enlarged scale.
Figure 11:
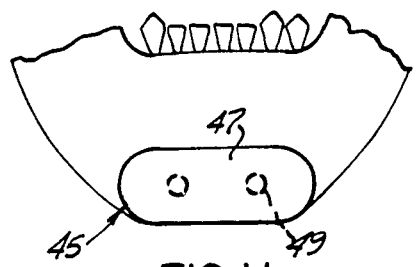
FIG. 11 is a fragmentary frontal view of the assembled implant with the mandible fragmentarily illustrated and corresponding to FIG. 10.

Thereafter the locking pin 31 is withdrawn from the bore 29 and the drill guide is removed from the exposed jaw mandible. Thereafter into each of the bores 37 there is manually threaded thereinto the headless self-threading cortical bone screws 39, FIGS. 6 and 7. These screws are preferably constructed of titanium, or stainless steel or any other biologically acceptable orthopedic material including chrome cobalt, for illustration.

The cortical screw 39 has an approximate diameter of 3 mm and a length of 9 mm, for illustration. Said screw has a longitudinal bore 41 approximately 5 mm in length and of a diameter of approximately 1.5 mm, for illustration.

The outer end of bore 41 of said screw terminates in a hex slot 43 which extends into the screw approximately 2 mm and is adapted to receive an Allen wrench or other tool by which the screw is rotated and fully threaded into the mandible bores 37.

The cortical screw 39 is headless and is threaded into the exposed mandible such sufficient distance within the bores 37 and under compression so that the outer ends of the screws are flush with the outer surface of the exposed jawbone, FIG. 10.

A further step includes assembling a resilient preformed chin implant 45 having a body of silicone rubber which is preferably molded, having a pair of embedded projecting mount posts or locator rods 49. The implant operatively bears against the exposed mandible bone, FIG. 10, and the corresponding mount posts loosely and guidably project into bores 41 of the cortical self threading screws 39. In the illustrative embodiment, the locator rods have a length of 5 mm adapted for a slip fit into the bores of said cortical screws.

Figure 9:
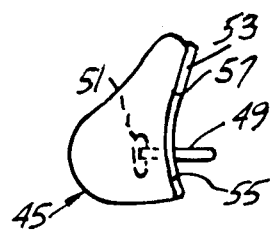
FIG. 9 is a side elevational view of a chin implant shown in FIG. 6, on an enlarged scale.

The respective locator posts 49 may be constructed of polyethylene, hard rubber or a suitable metal, such as stainless steel. Said posts include at their inner ends the head 51, FIG. 9, which is embedded within the implant body 47 in the forming or molding process.

A final step in the method of applying the chin implant includes returning the stripped tissue including lip and frontal chin tissue back into normal position and suturing it in place so as to enclose and retainingly engage implant 45 for the successive healing process which may take four to eight weeks, for illustration.

The front face 55 of the resilient implant 45 is of a curvature so as to generally register with the corresponding transverse curvature of the adjacent exposed mandible for snug registry therewith, FIG. 10. In the illustrative embodiment, there is applied to the front face 55 of said implant a layer of Dacron Velour facing 53 suitably bonded thereto as at 57.

Application of the Dacron Velour layer 53 to the front face 55 of the implant 45 provides for an improved implant assembly wherein during the healing process migrating tissue from the jawbone travels into the facing to provide a biomechanical interlock with the inner surface of the implant relative to the exposed jawbone.

In the initial step of stripping of tissue from the mandible, the lip and chin tissues are partly severed from the adjoining tissues down to the Mentum or to the bone surface at the anterior border of the mandibular jawbone.

The present invention is therefore primarily directed to the method of applying a chin implant to the human mandible and additionally the structure of the drill guide, the structure of the implant and a specific cortical screw for this purpose.

The locating posts or points 49 of the implant 45 may be of the same material as the implant or may be of metal such as stainless steel or titanium or may be constructed of a polyethylene.

The use of the present drill guide when properly located with respect to the median plane 22 of the mandible assures the guided drilling of a pair of bores 37 into the exposed jawbone which are accurately spaced apart 12 mm, for illustration, equidistant from said median plane and in the illustrative embodiment are at least 6 mm above the lower border of the mandible.

The construction of the present implant including the locating posts 49 which are nested within the bores 41 of the respective screws 39 provide the positive, accurate location of the implant centrally of the jaw and prevents transverse slipping or displacement once the healing process has been completed. The use of cortical screws 39 with their outer ends extending flush with the outer border of the mandible, as well as the use of the Dacron Velour layer on the facing side of the implant prevents the heretofore objectional bone resorption or migration of the chin implant into the bone of the mandible.

The use of the present Dacron Velour facing also provides for and prevents movement or migration of conventionally constructed implants into the bone of the mandible.

The present Dacron Velour layer also provides for and encourages integration and migration of adjacent mandible bone tissue into the facing, thereby providing a tissue biomechanical interlock with the chin implant tending to retain the implant in position against to the jawbone.

Figure 12:
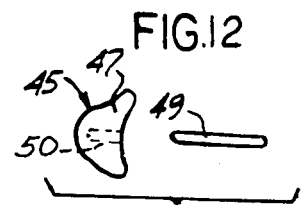
FIG. 12 is a side view of the chin implant of FIG. 6 with the mount post separate from the implant.

As shown in FIG. 12, the locator or mount posts 49 are separate from the chin implant 45, and are adapted for snug assembly into laterally spaced bores 50 therein. As a modification of the present method, after threading of the cortical screws 39 into bores 37, the mount posts 49 at their one ends are projected into the bores 49 of the cortical screws. Thereafter, a further step includes assembling the resilient preformed chin implant 45 snugly against the exposed jawbone with its bores 50 cooperatively and snugly receiving the other ends of the mount posts 49. The procedure can be reversed with the mount posts first snugly projected within corresponding bores 50 within the chin implant.

Having described my invention, reference should now be had to the following claims:

I claim:

1. The method of applying a chin implant to a human comprising;

surgically stripping tissue from frontal portions of the lower jaw mandible adjacent the chin down to the jaw bone;

centrally locating and applying an apertured drill guide to the exposed jawbone and to the undersurface of the chin with the central axis of the guide in alignment with a median plane of the mandible;

drilling through the guide a first bore into said jawbone at said median plane;

projecting a removable locking pin through the guide and snugly into said first bore for supporting and retaining the drill guide as centered;

successively drilling through said guide a pair of laterally spaced bores into said jawbone equidistant from said median plane;

upon removal of said locking pin and guide, manually threading into each of said pair of bores, a headless self threading cortical bone screw having an axial bore, with the outer end of said screw in registry with the outer surface of said jawbone;

assembling a resilient preformed chin implant with a pair of projecting mount posts snugly against said jawbone while slidably positioning said posts into said screws respectively;

and suturing the stripped tissue back into natural position enclosing and retaining engaging said implant.

2. The method of applying a chin implant to a human comprising;
surgically stripping tissue from frontal portions of the lower jaw mandible adjacent the chin down to the jawbone;
accurately drilling a pair of laterally spaced bores into said jawbone equidistant from a median plane of the mandible;
manually threading into each of said bores, a headless self threading cortical bone screw having an axial bore, with the outer end of said screw in registry with the outer surface of said jawbone;
assembling a resilient performed chin implant with a pair of projecting mount posts snugly against said jawbone while slidably positioning said posts into said screws respectively;
and suturing the stripped tissue back into natural position enclosing and retainingly engaging the implant.

3. In the method of claim 1, the screws being oversized relative to said bores, the threading of said screws into the jawbone being in compression.

4. In the method of claim 1, the drill guide snugly engaging the undersurface of the chin locating the pair of bores a predetermined distance from the bottom of the chin.

5. In the method of claim 1, the drill guide including a plurality of parallel spaced guide bores to receive a drill, accurately locating said pair of bores upon opposite sides of said median plane.

6. In the method of claim 1, said screws being selected from the group consisting of titanium, stanless steel and any biologically acceptable orthopedic material.

7. In the method of claim 1, the implant being selected from the group consisting of silicone rubber, polyethylene, hydroxylapatite and a biologically acceptable resilient material, said mount posts being selected from the group consisting of polyethylene, stainless steel, chrome cobalt and a biologically acceptable material compatible with the screws.

8. In the method of claim 1, the implant having a facing layer of Dacron Velour, the tissue of the bone migrating and biologically interlocking with the Velour facing.

9. In the method of claim 4, said drill guide including a pair of laterally spaced arcuate stabilizing arms cooperatively registering with the undersurface of said chin.

10. In the method of claim 2, the screws being oversized relative to said bores, the threading of said screws into the jawbone being in compression.

11. In the method of claim 2, said screws being selected from the group consisting of titanium, stainless steel and any biologically acceptable orthopedic material.

12. In the method of claim 2, the implant being selected from the group consisting of silicone rubber, polyethylene, hydroxylapatite and a biologically acceptable resilient material; said moutn posts being selected from the group consisting of polyethylene, stainless steel, chrome cobalt and a biologically acceptable material compatible with the screws.

13. In the method of claim 2, the implant having a facing layer of Dacron Velour, the tissue of said bone migrating and biologically interlocking with the Velour facing.

14. The method of applying a chin implant to a human comprising;
surgically stripping tissue from frontal portions of the lower jaw mandible adjacent the chin down to the jawbone;
centrally located and applying an apertured drill guide to the exposed jawbone and to the undersurface of the chin with the central axis of the guide in alignment with a median plane of the mandible;
drilling through the guide a first bore into said jawbone at said median plane;
projecting a removable locking pin through the guide and snugly into said first bore for supporting and retaining the drill guide as centered;
successively drilling through said guide a pair of laterally spaced bores into said jawbone equidistant from said median plane;
upon removal of said locking pin and guide, manually threading into each of said pair of bores, a headless self threading cortical bone screw having an axial bore, with the outer end of said screw in registry with the outer surface of said jawbone;
snugly assembling a pair of mount posts at their one ends into a pair of spaced apertures in a resilient preformed chin implant;
assembling the chin implant snugly against said jawbone with said posts at their other ends slidably positioned within said screws respectively;
and suturing the stripped tissue back into natural position enclosing and retainingly engaging said implant.

15. The method of applying a chin implant to a human comprising;
surgically stripping tissue from frontal portions of the lower jaw mandible adjacent the chin down to the jaw bone;
accurately drilling a pair of laterally spaced bores into said jawbone equidistant from a median plane of the mandible;
manually threading into each of said bores, a headless self threading cortical bone screw having an axial bore, with the outer end of said screw in registry with the outer surface of said jawbone;
snugly assembling a pair of mount posts at their one ends into a pair of spaced apertures in a resilient preformed chin implant;
assembling the chin implant snugly against said jawbone with said posts at their other ends slidably positioned within said screws respectively;
and suturing the stripped tissue back into natural position enclosing and retainingly engaging the implant.

* * * * *